US011026562B2

(12) United States Patent
Ulmschneider

(10) Patent No.: US 11,026,562 B2
(45) Date of Patent: Jun. 8, 2021

(54) ENDOSCOPE

(71) Applicant: Karl Storz SE & Co. KG, Tuttlingen (DE)

(72) Inventor: Daniel Ulmschneider, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 519 days.

(21) Appl. No.: 15/951,900

(22) Filed: Apr. 12, 2018

(65) Prior Publication Data

US 2018/0296072 A1 Oct. 18, 2018

(30) Foreign Application Priority Data

Apr. 13, 2017 (DE) .......................... 102017108029.5

(51) Int. Cl.
| | | |
|---|---|---|
| *A61B 1/00* | (2006.01) | |
| *A61B 1/04* | (2006.01) | |
| *A61B 5/03* | (2006.01) | |
| *G02B 23/24* | (2006.01) | |
| *H01R 13/52* | (2006.01) | |

(Continued)

(52) U.S. Cl.
CPC ...... *A61B 1/00071* (2013.01); *A61B 1/00013* (2013.01); *A61B 1/00124* (2013.01); *A61B 1/00126* (2013.01); *A61B 1/00165* (2013.01); *A61B 1/00167* (2013.01); *A61B 1/04* (2013.01); *A61B 5/036* (2013.01); *G02B 23/2461* (2013.01); *A61B 1/05* (2013.01); *A61B 1/126* (2013.01); *A61B 5/0084* (2013.01);

(Continued)

(58) Field of Classification Search
CPC ............ A61B 1/00071; A61B 1/00013; A61B 1/00018; A61B 1/00112; A61B 1/00114; A61B 1/00165; A61B 1/042; A61B 1/05; A61B 1/051
See application file for complete search history.

(56) References Cited

U.S. PATENT DOCUMENTS

| | | | |
|---|---|---|---|
| 4,569,335 A | 2/1986 | Tsuno | |
| 4,854,302 A * | 8/1989 | Allred, III | ............. A61B 1/042 |
| | | | 600/109 |

(Continued)

FOREIGN PATENT DOCUMENTS

| | | |
|---|---|---|
| DE | 102013202037 A1 | 8/2014 |
| DE | 102013207109 A1 | 11/2014 |

(Continued)

OTHER PUBLICATIONS

German Search Report Application No. DE102017108029.5 dated Nov. 17, 2017 12 pages.

(Continued)

*Primary Examiner* — Aaron B Fairchild
(74) *Attorney, Agent, or Firm* — Whitmyer IP Group LLC

(57) ABSTRACT

An endoscope has an elongate shaft, with a housing that is arranged in the endoscope and has a fluid-tight embodiment and a sensor for capturing a physical measurement variable, the sensor being arranged in the shaft. The sensor is situated outside of the fluid-tight housing. A signal line extends from the sensor to a coupling point at the fluid-tight housing. The coupling point connects the signal line to an evaluation unit that is arranged in an interior of the housing for the purposes of evaluating the measurement signal.

13 Claims, 2 Drawing Sheets

(51) Int. Cl.
*A61B 5/00* (2006.01)
*A61B 1/05* (2006.01)
*A61B 1/12* (2006.01)

(52) U.S. Cl.
CPC ........ *A61B 5/6847* (2013.01); *G02B 23/2476* (2013.01); *H01R 13/5224* (2013.01)

(56) References Cited

U.S. PATENT DOCUMENTS

| | | | |
|---|---|---|---|
| 2005/0075539 A1* | 4/2005 | Schulz | A61B 1/00016 600/160 |
| 2008/0200758 A1* | 8/2008 | Orbay | A61B 1/00066 600/112 |
| 2012/0029287 A1* | 2/2012 | Wieters | H01B 17/305 600/133 |
| 2014/0316194 A1 | 10/2014 | Rapp et al. | |
| 2017/0280982 A1* | 10/2017 | Kugimiya | G02B 23/2484 |

FOREIGN PATENT DOCUMENTS

| | | |
|---|---|---|
| DE | 102015000773 A1 | 7/2016 |
| DE | 102015015993 A1 | 6/2017 |
| EP | 1522253 A1 | 4/2005 |

OTHER PUBLICATIONS

Extended European Search Report Application No. EP 18 16 5832 dated Sep. 20, 2018 7 pages.

\* cited by examiner

ENDOSCOPE

TECHNICAL FIELD

The present invention relates to an endoscope having a shaft, in which a sensor is arranged for capturing a physical measurement variable.

BACKGROUND

These days, endoscopes find use in many applications in medicine and technology. An endoscope typically comprises a rigid, semi-rigid or flexible elongate shaft, which is suitable for insertion into a cavity. An endoscope objective for producing an image of an object field in the cavity is arranged in the distal (i.e. observer-distant) end region of the shaft, said endoscope objective comprising at least one lens. The endoscopic image can be transmitted to the proximal (observer-near) end of the endoscope by way of optical or electronic means that are arranged in the interior of the shaft, said endoscopic image being available at said proximal end for observation by, or a display for, a user. Since, as a rule, sufficient light is not present in the observed cavity, an illumination light guide, furthermore, is often arranged within the shaft in order to transport illumination light to the distal end of the endoscope, where it is used to illuminate the cavity. For the purposes of introducing illumination light into the endoscope, a connector for connecting an optical cable is often present in the vicinity of the proximal end, it being possible to supply the illumination light from a separate light source by means of said optical cable.

In the case of modern video endoscopes, one or more image sensors for recording an image produced by the objective are frequently arranged at the distal end. Alternatively, the image sensors may also be arranged at the proximal end of the endoscope, for example in a handle. In order to facilitate cleaning of the video endoscope, for example in an autoclave, said video endoscope can have a fluid-tight, in particular gas-tight embodiment. In this way, the electronic parts present, such as image sensors, cables and circuit boards, are protected against entering moisture.

Within the scope of performing an endoscopic operation, and also for diagnostic purposes, it may be necessary to measure the pressure of a fluid in the body cavity observed by the endoscope. Thus, for example, an insufflation gas or rinsing liquid can be introduced into the body cavity in order to create sufficient workspace for endoscopic manipulations or for cleaning an operating region and facilitating an unimpeded endoscopic sight. For the purposes of performing the insufflation or the rinse in a reliable and sparing manner, measuring the pressure prevalent in the body cavity in the process is advantageous. Likewise, capturing a pressure in the cavity into which the shaft has been introduced may be desirable in technical applications.

U.S. Pat. No. 4,569,335 has disclosed a fiberscope, having a shaft in which illumination light guides and a fiber-optic pressure sensor are provided.

EP 1522253 A1 discloses an electronic endoscope having a shaft and a proximal handle, wherein provision is made of a distal image sensor, the signals of which are guided via electrical lines to an evaluation unit that is situated in the handle. The endoscope may be hermetically sealed to allow autoclaving thereof.

DE 102015000773 A1 discloses an endoscope having a light guide bundle, wherein a fiber-optic pressure sensor is arranged in the light guide bundle.

A disadvantage of these instruments known from the prior art is that, firstly, the signal of a sensor for measuring a physical variable, such as a pressure sensor, has to be led out of the endoscope via a separate line and has to be supplied to an external processing unit. Secondly, the entire endoscope has to be sealed to allow good cleaning thereof, meaning significant outlay.

SUMMARY

It is therefore an object of the present invention to provide an endoscope having a sensor for capturing a physical measurement variable, wherein the endoscope can evaluate the sensor signal and said endoscope can be cleaned well at the same time.

This object is achieved by an apparatus according to the invention.

An endoscope comprises an elongate shaft that may have a rigid, flexible or semi-flexible embodiment. The shaft is embodied to be inserted into a cavity, for example into a body-internal cavity of a human or animal body, or into a cavity of a technical object, and, in particular, has a length suitable to this end and a corresponding diameter. In particular, the endoscope is a video endoscope having one or more image sensors that may be arranged in a distal or proximal region of the endoscope. In order to protect the sensitive components of the endoscope from moisture entering during the application and during cleaning, a fluid-tight, in particular gas-tight housing is provided in the endoscope. The housing can surround the image sensors, lines or else circuit boards with further electronic components.

In order to be able to capture a physical variable, the endoscope has a corresponding sensor. This may be a sensor for measuring a temperature, a pressure sensor or any other sensor. The endoscope may also have a plurality of sensors. The sensor may comprise electronic semiconductor components. The pressure sensor may be embodied as a fiber-optic pressure sensor. In order to be able to reliably capture a physical variable, for example in the surroundings of the endoscope, the sensor is situated outside of the fluid-tight housing. In this way, physical conditions, which should be captured by measurement, act on the sensor. A signal line extends away from the sensor, said signal line transmitting the measurement signals produced by the sensor. These may be electrical signals with an appropriately embodied signal line or this can relate to optical signals that are guided by way of an optical line such as an optical fiber. Therefore, the signal line can be embodied, at least in portions, for transmitting electrical signals. If the sensor is a fiber optic pressure sensor, the signal line is embodied, at least in portions, as an optical fiber. The signal line may also be an optical line in one portion and an electrical line in another portion, for example if an optical signal is converted into an electrical signal, or vice versa, between the portions.

In order to be able to undertake an evaluation of the signals provided by the sensor already in the endoscope itself, the endoscope has an appropriate electronic evaluation unit. The evaluation unit is arranged in an interior of the fluid-tight housing, optionally together with other electronic components. The signal line extends from the sensor to a coupling point at the housing and it is further connected to the evaluation unit.

Further, the endoscope may have a handle that is arranged at the proximal end of the shaft. By way of example, the handle serves to allow a user to grip and operate the endoscope. It may have operating buttons, levers or valves for controlling the various functions of the endoscope. In particular, the fluid-tight housing may be arranged, at least in part, within the handle. Electronic components within the housing often produce heat, which can then be dissipated via the handle. Dissipating heat at a distal end of the endoscope is usually not desired in order not to heat, and consequently possibly damage, an observed cavity.

The coupling point is preferably arranged at the housing in the region of the handle. More space is available there than in the shaft, and so the signal line can be guided into the interior of the housing at this point.

The shaft of the endoscope has an outer wall, with the signal line, at least in portions, extending between the outer wall and the housing with the fluid-tight embodiment. In particular, the signal line extends through the shaft up into the region of the proximal handle and to the coupling point.

Moreover, fibers for transporting light can be arranged between the outer wall and the fluid-tight housing. By way of example, these are fed by an external light source or a light source that is situated in the handle and these transport the light to the distal end of the endoscope in order to illuminate the cavity there. Here, the sensor and/or the signal line can be embedded, at least in portions, between the fibers. To this end, provision can be made of, for example, a channel between the optical fibers, in which the sensor and/or signal line are arranged. Sensor and signal line can also be adhesively bonded to the optical fibers. This arrangement is advantageous in that the sensor or the signal line can be housed in the endoscope shaft in a space-saving manner, without increasing the diameter of the endoscope since the room provided for the illumination fibers in any case is also used.

The signal line is guided into the interior of the fluid-tight housing at the coupling point. The signal line can be guided through the coupling point without interruption and connected to the evaluation unit in the interior. Alternatively, one portion of the signal line may also end at the coupling point and a further portion may connect the coupling point to the evaluation unit in the interior. The evaluation unit may also be arranged directly behind the coupling point in the interior of the housing, and so there is a direct connection to the signal line in the region of the coupling point. The portions of the line can be electrical or optical guides in each case.

The coupling point can have a plug or a socket for connecting to the signal line and for transmitting electrical or optical signals, at the side facing the interior or the opposite side, or at both sides. To this end, the signal line can be provided with complementary plugs or sockets. Plugs and sockets can have conducting contacts for transmitting electrical signals in a manner known per se. Alternatively, these can be fiber plugs or sockets, such as optical waveguide connectors, which are able to connect light guides by optical means. In this way, it is possible to ensure a simple, reliable connection of the signal line or of the portions of the signal line to the coupling point, which moreover simplifies the production, as the lines only have to be plugged in.

The coupling point has a fluid-tight, in particular gas-tight embodiment. This ensures that no moisture can enter into the interior of the housing in the region of the coupling point as a result of cleaning or during the application. To this end, the coupling point may have a seal. By way of example, a passed signal line may be connected to the housing in the region of the coupling point by means of an adhesive such as an artificial resin. Alternatively, provision can be made of a flexible polymer seal, through which the signal line is guided. If plugs or sockets are provided, these may have a sealed embodiment made of non-permeable material and may be connected to the housing in a sealing manner. To this end, embedding electrical contacts in a sealing material, for example in the form of a glass-sealed plug, is known.

The evaluation unit that is arranged in the fluid-tight housing obtains signals from the sensor and evaluates these. Here, these can be electrical signals that are produced by a change in voltage or resistance in the sensor, for example. For the purposes of the evaluation, the evaluation unit has appropriate electrical circuits that process the electrical measurement signal. As required, the signals may be amplified or converted. Additionally, the evaluation unit may have electronic components for in-depth signal processing. The signals can be corrected and, to this end, be synced to one another or to other measurement signals. By way of example, the measurements of a pressure sensor, which may be temperature-dependent, could be corrected by the measurements of a temperature sensor or measurement values could be adapted by computation. The evaluation unit may have a processor, random access memory or data memory.

Measurement signals can be stored by the evaluation unit for certain period of time and can then be processed further or transmitted on. Additionally, the evaluation unit can be embodied to identify a sensor that transmits signals in order to be able to distinguish the signals of different sensors from one another. If need be, means for supplying the sensor with power may be provided in the housing.

If this is a fiber-optic sensor, the signals of which are transmitted to the evaluation unit via the signal line, the evaluation unit can have means for capturing and evaluating the optical signals. These can be spectrometers, interferometers, optical gratings or light sensors and optoelectric transducers. The evaluation unit may have a light source for feeding the fiber-optic sensor. In this case, too, electronic components may be present, as explained above in relation to the electrical signals. Moreover, the signals of further sensors can also be processed in the evaluation unit and the results can be compared to one another and evaluated.

The evaluation of the measurement signals in an evaluation unit in the endoscope itself is advantageous in that the signal line itself need not be guided out of the instrument. Additionally, it is possible to dispense with an additional external evaluation unit, making the arrangement particularly compact.

Further, the endoscope may have a line that is connected to the evaluation unit and that is suitable for guiding signals or data with the result of the evaluation from the evaluation unit to a monitor or a medical device that is arranged outside of the endoscope. Endoscopes, in particular video endoscopes, often already have a line which supplies the video endoscope with power and which guides signals and data, for example from an image sensor of the endoscope to an external device for further processing or directly to a monitor for displaying the data. Ideally, use can be made of a line that is already present in order, also, to transmit the signals or data of the evaluation unit of the sensor to the outside. By way of example, an already evaluated measurement result can be displayed directly on a monitor or it can be transmitted for further consideration to a medical device, for example for regulating the pressure of an insufflation or liquid pump. Then, no further line, which would make the handling of the video endoscope more difficult, is necessary. This can be realized particularly easily if the evaluation unit and an image sensor, and/or the means for processing an image signal, together are situated in the housing in the region of the handle. They may be arranged on the same printed circuit board and the signals and data of the evaluation unit and of the image processing can be guided to the outside together by way of the available line.

Alternatively, or additionally, the endoscope has a transmitter that is connected to the evaluation unit and that is suitable for transmitting signals or data with the result of the evaluation wirelessly from the evaluation unit to a monitor or a medical device that is arranged outside of the endoscope. This can be effectuated in a manner known per se by way of electromagnetic waves (WLAN, Bluetooth or other known methods). An external device or a monitor have a reception unit in order to receive the signals and in order to directly display or further process a measurement result.

BRIEF DESCRIPTION OF THE DRAWINGS

Further aspects of the invention emerge from the following description of the preferred exemplary embodiments and from the attached drawings. In the drawings.

DETAILED DESCRIPTION

Figure 1:
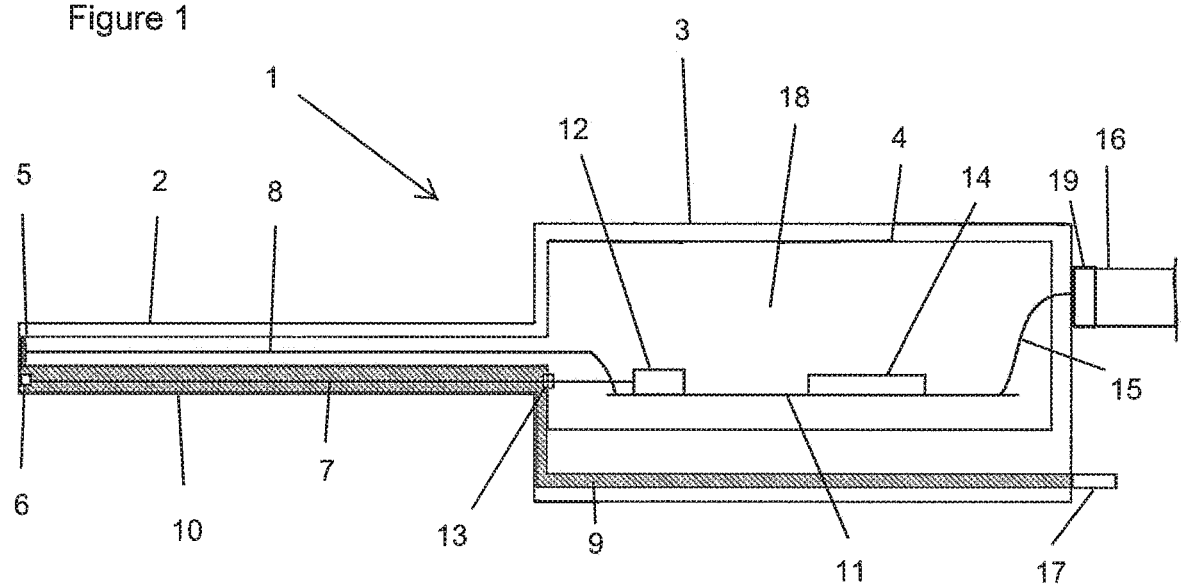
FIG. 1 shows an exemplary embodiment of an endoscope according to the invention in a longitudinal section.

The endoscope 1 according to the invention, illustrated in FIG. 1, is a video endoscope and it has a shaft 2 and a handle 3 that adjoins the shaft at the proximal end. An autoclave-tight (i.e. fluid-tight, in particular gas-tight) housing 4 extends in the interior of the handle 3 and of the shaft 2. An image recorder 5 consisting of an image sensor and an objective arranged in front thereof is situated at the distal end of the housing 4. Light reaches into the shaft 2 and the housing 4 from the distal end through a window and said light is imaged on the image sensor by the objective. A data line 8 guides the data produced by the image sensor further in the proximal direction to a circuit board 11 placed inside the housing 4. An image-processing unit 14 is assembled on the circuit board, said image-processing unit preparing the data received by the image sensor for the transmission out of the endoscope 1. The housing 4 is sealed on all sides, and so no moisture enters into the housing 4 if high atmospheric pressure and moisture impinges on the endoscope 1, as is the case during cleaning in an autoclave. To this end, the distal window can be sealed accordingly in relation to the shaft 2, for example it can be soldered therein. In this way, the housing 4 protects the electronic components on the circuit board 11, the image recorder 5 and the line 8 within the housing 4.

Outside of the housing 4, there is, distally in the shaft, a pressure sensor 6, the pressure-sensitive area of which is connected to the surroundings of the endoscope 1 such that an ambient pressure can be measured. From the pressure sensor 6, a signal line 7 extends through the shaft 2 to a coupling point 13 at the housing 4. The coupling point 13 is situated in the region of the distal end of the handle 3 at the housing 4 with the fluid-tight embodiment in this exemplary embodiment. Here, the signal line 7 extends between an outer wall 10 of the shaft 2 and the housing 4. Optical fibers 9 are arranged around the pressure sensor 6 and the signal line 7, and surround said pressure sensor and signal line. Said optical fibers extend as far as a proximal light connector 17, at which an optical cable for connecting to an external light source can be connected (not illustrated here).

At the coupling point 13, the signal line 7 is guided into the interior 18 of the housing 4. The coupling point 13 has an autoclave-tight embodiment; i.e., as explained above, no vapor can enter into the housing 4 when the endoscope 1 is autoclaved. In the housing 4, the signal line 7 extends to an evaluation unit 12 that is assembled on the circuit board 11. Consequently, the signals of the pressure sensor 6 are guided, via the signal line 7, into the housing 4 through the shaft 2 and to the evaluation unit 12. The evaluation unit 12 has a number of circuits, a processor, random access memory and data memory (not illustrated here). It evaluates the electrical or optical signals obtained from the sensor 6 and prepares said signals for the display at an external monitor 42.

The evaluation unit 12 and image-processing unit 14 are situated on the same circuit board 11. The latter is connected to a video cable 16 attached outside of the endoscope 1 by way of a connection 15 and an interface (not illustrated here). The video cable 16 connects the endoscope 1 to a control unit 41 and, in the further extent, to the external monitor 42, as illustrated in more detail in FIG. 4. Thus, both the results of the evaluation of the sensor signal obtained by the evaluation unit 12 and the data of the image-processing unit 14 are guided from the endoscope 1 to a monitor via the video cable 16. In this way, the number of cables connected to the endoscope 1 is reduced to a minimum. Alternatively, the monitor 42 may also be attached directly to the proximal end of the endoscope 1 instead of the video cable 16 and said monitor can receive the data from the evaluation unit 12 and the image-processing unit 14.

In the present example, the endoscope 1 moreover additionally has a transmitter 19 at the interface to the video cable 16. Said transmitter is embodied to wirelessly transmit the data and signals provided by the evaluation unit 12 and the image-processing unit 14 to an external receiver unit that belongs to a monitor or a medical device, for example. In this way, it is possible to omit the cable 16 in the entirety thereof where necessary, improving the handling of the endoscope 1. Then, the endoscope 1 has a dedicated energy source (not illustrated here).

Figure 2:
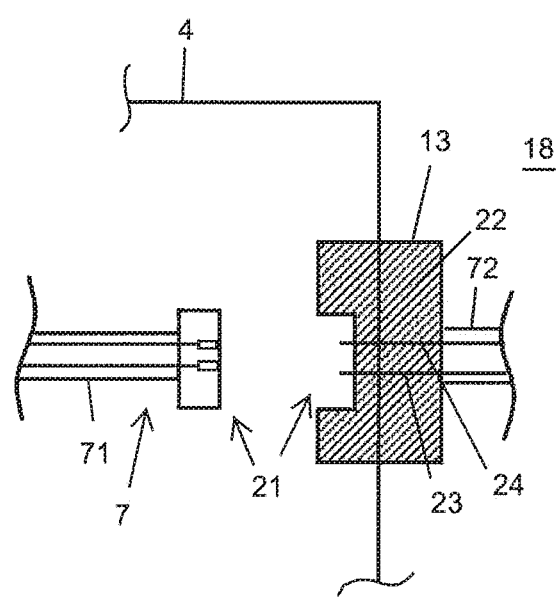
FIG. 2 shows an exemplary embodiment of a coupling point.

FIG. 2 shows a possible configuration of a coupling point 13, as may be used in an endoscope 1 according to FIG. 1.

The coupling point 13 is situated on a portion of the housing 4 within the endoscope 1. It is embodied as a plug-in connection 21 and has a socket with two contacts 23 and 24 at the outer side of the housing 4. A first portion 71 of the signal line 7, which is embodied as an electrical signal line in this case, has a plug at its end, said plug having a complementary embodiment to the socket at the coupling point 13. The contacts 23 and 24 are embedded in a seal 22 and said contacts extend through the seal 22 and the housing wall 4 to a side of the coupling point 13 that is situated in the interior 18 of the housing 4. In particular, the coupling point 13 is embodied as a glass-sealed plug. The latter has a sealed connection to the housing 4. In the interior 18, the contacts 23 and 24 are guided on within a second portion 72 of the signal line 7, which is securely connected to the coupling point 13. Within the further extent, the second portion 72 is connected to the evaluation unit 12 and it transmits to the evaluation unit 12 the signals that were transmitted from the pressure sensor 6 via the first portion 71 of the signal line 7 and the coupling point 13. The plug-in connection may also have a plurality of contacts, depending on how many contacts are required for the signal transmission.

Figure 3:
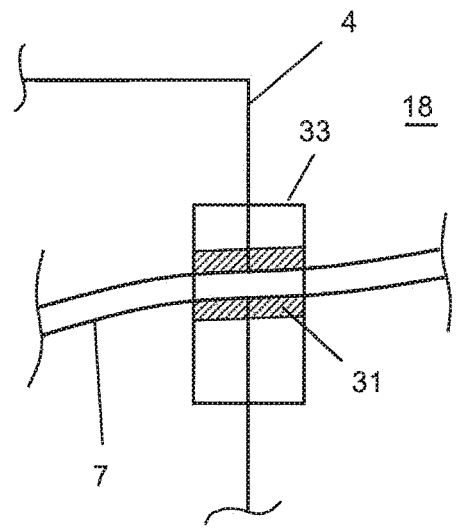
FIG. 3 shows a further exemplary embodiment of a coupling point.

FIG. 3 illustrates an alternative configuration of a coupling point 33, as may be used in an endoscope 1 according to FIG. 1.

As previously, the coupling point 33 is situated at a portion of the housing 4 within the endoscope 1. It is embodied as a feed-through, which extends from outside of the housing 4 to the interior 18 through the coupling point 33. The signal line 7 is guided without interruption through the coupling point 33 and it contacts the evaluation unit 12 in the interior 18, as explained above. In order to guarantee that the coupling point 33, and hence the housing 4, has a gas-tight embodiment, the signal line 7 is adhesively bonded into the coupling point 33 in the area thereof; i.e., said signal line is surrounded by an adhesive 31. Here, the signal line 7 is an optical cable, for example, which extends from a fiber-optic pressure sensor 6 to the evaluation unit 12.

Figure 4:
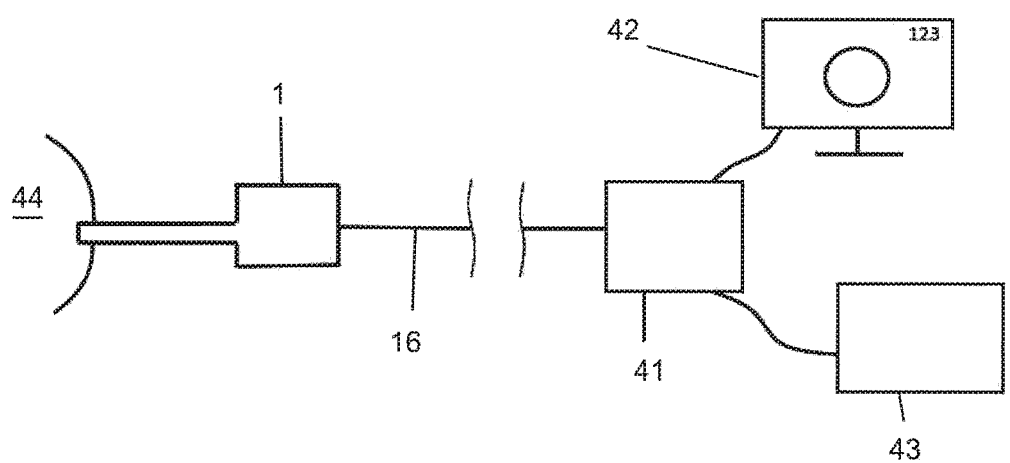
FIG. 4 shows a medical system having an endoscope.

FIG. 4 shows a system in which an endoscope according to the invention can be arranged. By way of a video cable 16, the endoscope 1 is connected to a CCU (camera control unit, abbreviated CCU) 41. The latter receives the video data from the endoscope 1 and processes said video data for displaying the video on the connected monitor 42. The data of the sensor 6 and of the evaluation unit 12 are likewise transmitted to the CCU 41 and, onward, to the monitor 42 via the video cable 16. In the present example of a pressure sensor 6, a pressure measured in a body cavity 44 is displayed on the monitor 42. Moreover, an insufflation pump 43 is also connected to the CCU 41. Said insufflation pump likewise receives the data from the sensor 6 and/or the evaluation unit 12. With the aid of the information about the current pressure in the body cavity 44 obtained thus, it is possible to control the insufflation pump 43 and adapt the pressure according to requirements.

What is claimed is:

1. An endoscope comprising:
   an elongate shaft,
   a housing that is arranged in the endoscope and is fluid-tight,
   an image sensor that is arranged within the fluid-tight housing,
   pressure a sensor for capturing a physical measurement variable, said pressure sensor being arranged in the shaft,
   the pressure sensor being situated outside of the fluid-tight housing, and
   a signal line that extends from the pressure sensor to a coupling point at the fluid-tight housing,
   wherein the coupling point connects the signal line to an interior of the fluid-tight housing and the signal line is connected to an evaluation unit that is arranged in the interior.

2. The endoscope as darned in claim 1, wherein the sensor is a fiber-optic pressure sensor, wherein the signal line, at least in portions, is embodied as an optical fiber.

3. The endoscope as claimed in claim 1, wherein the signal line, at least in portions, is embodied to transmit electrical signals.

4. The endoscope as claimed in claim 1, wherein the endoscope has a handle that is arranged at a proximal end of the shaft and the fluid-tight housing is arranged, at least in part, within the handle.

5. The endoscope as claimed in claim 4, wherein the coupling point is arranged at the housing in a region of the handle.

6. The endoscope as claimed in claim 1, wherein the shaft has an outer wall and the signal line, at least in portions, extends between the outer wall and the fluid-tight housing.

7. The endoscope as claimed in claim 1, wherein the shaft has an outer wall and fibers for transporting light are arranged between the outer wall and the fluid-tight housing, wherein the sensor and/or the signal line, at least in portions, is embedded between the fibers.

8. The endoscope as claimed in claim 1, wherein, for transmitting electrical or optical signals, the coupling point has a plug or a socket for connecting to the signal line.

9. The endoscope as claimed in claim 1, wherein the coupling point is fluid-tight.

10. The endoscope as claimed in claim 1, wherein the evaluation unit evaluates the signals obtained by the pressure sensor.

11. The endoscope as claimed in claim 10, wherein the endoscope has a line that is connected to the evaluation unit and that is suitable for guiding signals or data with the result of the evaluation from the evaluation unit to a monitor or a medical device that is arranged outside of the endoscope.

12. The endoscope as claimed in claim 11, wherein the endoscope has a transmitter that is connected to the evaluation unit and that is suitable for wirelessly transmitting signals or data with the result of the evaluation from the evaluation unit to a monitor or a medical device that is arranged outside of the endoscope.

13. The endoscope as claimed in claim 10, wherein the endoscope has a transmitter that is connected to the evaluation unit and that is suitable for wirelessly transmitting signals or data with the result of the evaluation from the evaluation unit to a monitor or a medical device that is arranged outside of the endoscope.

* * * * *

UNITED STATES PATENT AND TRADEMARK OFFICE
CERTIFICATE OF CORRECTION

Page 1 of 1

PATENT NO.         : 11,026,562 B2
APPLICATION NO.    : 15/951900
DATED              : June 8, 2021
INVENTOR(S)        : Daniel Ulmschneider It is certified that error appears in the above-identified patent and that said Letters Patent is hereby corrected as shown below:

In the Claims

Column 7, Line 41: Claim 1:
"pressure a sensor"
Should Read:
--a pressure sensor--

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*